(12) United States Patent
Gundling et al.

(10) Patent No.: US 10,041,061 B2
(45) Date of Patent: Aug. 7, 2018

(54) FUNGAL NUCLEIC ACID EXTRACTION

(75) Inventors: Gerard Gundling, Lake Forest, IL (US); Thomas Laffler, Vista, CA (US); Cristina A. Ivy, San Jose, CA (US); Lendell Cummins, San Diego, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 524 days.

(21) Appl. No.: 13/876,144

(22) PCT Filed: Sep. 23, 2011

(86) PCT No.: PCT/US2011/052871
§ 371 (c)(1),
(2), (4) Date: Aug. 16, 2013

(87) PCT Pub. No.: WO2012/050787
PCT Pub. Date: Apr. 19, 2012

(65) Prior Publication Data
US 2013/0323815 A1   Dec. 5, 2013

Related U.S. Application Data

(60) Provisional application No. 61/387,848, filed on Sep. 29, 2010.

(51) Int. Cl.
*C12N 1/06* (2006.01)
*C12N 15/10* (2006.01)

(52) U.S. Cl.
CPC .......... *C12N 15/1003* (2013.01); *C12N 1/06* (2013.01); *C12N 1/066* (2013.01)

(58) Field of Classification Search
USPC ................. 435/18, 23, 270, 306.1
See application file for complete search history.

(56) References Cited

U.S. PATENT DOCUMENTS

| | | | |
|---|---|---|---|
| 4,931,390 A | 6/1990 | Recsei | |
| 2004/0002592 A1* | 1/2004 | Einsele et al. | 536/23.1 |
| 2008/0193912 A1* | 8/2008 | Fong et al. | 435/2 |
| 2013/0059290 A1* | 3/2013 | Armes | 435/5 |

OTHER PUBLICATIONS

Szweda, P. et al. Lysostaphin—Sources and Applications. Biotechnologia 4(71)28-45, 2005.*
Scott J. et al. Lyticase: Endoglucanase and Protease Activities That Act Together in Yeast Cell Lysis. J of Bacteriology 142(2)414-23, May 1980.*
International Search Report and Written Opinion for Application No. PCT/US2011/052871, dated Jan. 27, 2012, 8 pages.
Karakousis A., et al., "An Assessment of the Efficiency of Fungal DNA Extraction Methods for Maximizing the Detection of Medically Important Fungi using PCR," Journal of Microbiological Methods, 2006, vol. 65 (1), pp. 38-48.
Schmale D.G., et al., "Mycotoxins in Crops: A Threat to Human and Domestic Animal Health," The Plant Health Instructor, American Phyiopathological Society, 2009, DOI: 10.1094/PHI-I-2009-0715-01.

* cited by examiner

*Primary Examiner* — Ralph J Gitomer
(74) *Attorney, Agent, or Firm* — Casimir Jones, S.C.; David Casimir

(57) ABSTRACT

The invention provides methods for extraction of fungal (e.g., yeast spp., filamentous fungal spp.) nucleic acid (e.g., DNA, RNA) from a sample (e.g., be human or veterinary clinical or research samples, agricultural samples, agricultural commodity samples, food products, or environmental samples). In some embodiments, the present invention provides enhanced nucleic acid extraction from samples comprising fungal cell(s) wherein enzymatic (e.g., lysostaphin treatment, lyticase treatment) sample treatment is performed in combination with mechanical (e.g., bead beating) sample treatment.

12 Claims, 3 Drawing Sheets

FIGURE 1

FUNGAL NUCLEIC ACID EXTRACTION

CROSS REFERENCE TO RELATED APPLICATIONS

The present Application is a national phase application under 35 U.S.C. § 371 of PCT International Application No. PCT/US2011/052871, filed on Sep. 23, 2011, which claims priority to U.S. Provisional Application Ser. No. 61/387,848 filed Sep. 29, 2010, the entirety of which is herein incorporated by reference.

FIELD OF THE INVENTION

The invention provides methods for extraction of fungal (e.g., yeast spp., filamentous fungal spp.) nucleic acid (e.g., DNA). In some embodiments, the present invention provides enhanced nucleic acid extraction from samples comprising fungal cell(s) wherein enzymatic (e.g., lysostaphin treatment, lyticase treatment) sample treatment is performed in combination with mechanical (e.g., bead beating) sample treatment.

BACKGROUND OF THE INVENTION

Numerous diseases result from fungal pathogens, including but not limited to fungal pneumonia (caused by species such as *Histoplasma capsulatum, Coccidioides immitis, Blastomyces dermatitidis*, and *Paracoccidioides brasiliensis*), opportunistic pulmonary fungal infections (due to, e.g., *Candida* species, *Aspergillus* species, *Mucor* species, and *Cryptococcus neoformans*) such as invasive aspergillosis, allergic fungal sinusitis, mucormycosis, and fungal keratitis of the skin or eyes. Additionally, numerous fungal species are capable of causing spoilage or mycotoxin contamination of foodstuffs due to infestation occurring prior to harvest, in stored materials such as grain, or during contamination of finished products. For example, the Food and Agriculture Organization has estimated that 25% of the world's crops are affected by mycotoxins each year, with annual losses of approximately 1 billion metric tons of foods and food products (Schmale et al. (2009) Mycotoxins in Crops: A Threat to Human and Domestic Animal Health, The Plant Health Instructor, American Phytopathological Society DOI: 10.1094/PHI-I-2009-0715-01).

In order to lessen the burden of human, animal, and plant fungal pathogens, it is necessary to detect evidence of fungal contamination or infection with high sensitivity. As fungal nucleic acid can be useful as an indicator of fungal contamination or infection, methods for efficient extraction of fungal nucleic acid are particularly desirable. However, standard methods for nucleic acid extraction result in notoriously poor yield when used for samples containing fungal species, particularly filamentous fungal species. Such low yield can be due to recalcitrance of the fungal cell wall to disruption.

Better methods are needed for fungal nucleic acid extraction.

SUMMARY OF THE INVENTION

The invention provides methods for extraction of fungal (e.g., yeast spp., filamentous fungal spp.) nucleic acid (e.g., DNA, RNA). In some embodiments, the present invention provides enhanced nucleic acid extraction from samples comprising fungal cell(s) wherein enzymatic (e.g., lysostaphin treatment, lyticase treatment) sample processing is performed in combination with mechanical (e.g., bead beating) sample processing.

In experiments conducted during the course of developing some embodiments of the present invention, it was found that pre-treatment of samples (*Candida albicans* or *Staphylococcus aureus* diluted in whole blood) with lyticase and lysostaphin followed by mechanical disruption using bead beating resulted in an eight-fold increase in the amount of fungal DNA extracted, as measured by quantitative PCR.

Accordingly, methods of the present invention find use in extraction of fungal nucleic acids (e.g., DNA, RNA) from samples using enzymatic treatment in combination with mechanical treatment. Such methods find use in, e.g., detecting fungal infection (for example, in human clinical settings, in veterinary settings, in research settings) or fungal contamination (e.g., of plants, of plant-based commodities or products, of environmental samples). Methods of the present invention also find use in research applications wherein extraction or preparation of fungal nucleic acids (e.g., DNA, RNA) is desired.

Methods of the present invention are not limited by the type of mechanical processing. In some embodiments, mechanical processing (e.g., disruption) includes but is not limited to particle-based disruption (e.g., homogenization using beads, microparticles, and the like, also referred to as bead beating), grinding, sonication, extrusion, freezing, freeze-thawing, high pressure and/or temperature, low pressure and/or temperature, and/or use of hammer mills, knife mills, ball mills, homogenizers (e.g., Dounce homogenizers), French press, chipping machines, grinding machines, extrusion devices, and/or irradiation. In some embodiments, bead beating is used. In some embodiments, more than one type of mechanical treatment may be used. Methods of the present invention are not limited by the type of particle used for mechanical disruption (e.g., bead beating). Particle materials include but are not limited to silica, minerals, glass, zirconia (zirconium)/silica, zirconia (zirconium)/yttrium, zirconia (zirconium), polymer (e.g., plastics, polycarbonate), garnet. Particles may be acid washed. Methods of the present invention are not limited by the size of particle used for mechanical disruption (e.g., bead beating). Sizes of particles include but are not limited to less than 0.1 mm, 0.1-0.5 mm, 0.5-1.0 min, 1.0-1.5 mm, 1.2-2 mm, 2-3 mm, 3-4 mm, 4 mm diameter or larger. Methods of the present invention are not limited by the conditions used for mechanical disruption (e.g., duration of mechanical disruption; number of repetitions; speed of disruption; vigor of disruption; etc.) The duration of mechanical disruption (e.g., bead beating) may be less than 1 sec, 1-5 sec, 5-10 sec, 10-25 sec, 25-60 sec, 1 min-2 min, 2 min-5 min, 5 min or longer. The number of repetitions of mechanical disruption (e.g., number of bead beating sessions) may be 2, 3, 4, 5, 6, 7, 7-10, 10 or more repetitions. The speed of disruption (e.g., speed or setting for bead beating) may be less than 50, 50-100, 100-250, 250-500, 500-750, 750-1000, 1000-1500, 1500-2000, 2000 or more rotations (oscillations) per minute. Mechanical processing may be in combination with one or more other sample treatments. Examples of sample treatments include but are not limited to heat treatment, cold treatment (e.g., chilling or freezing samples before, after, or between mechanical processing steps), stirring, rocking, vortexing, shaking, etc.

Methods of the present invention are not limited by type of enzymatic treatment. Enzymes used for sample treatment include but are not limited to lysostaphin, lyticase, zymolyase, chitinase, glucanase, endoglucanase, and protease.

Methods of the present invention are not limited by the nature of enzyme used for enzymatic treatment (e.g., recombinant enzyme, non-recombinant enzyme, crude enzyme, partially purified enzyme, homogenously purified enzyme) nor its level of activity (e.g., level of specific activity).

In some embodiments, methods of the present invention may involve dilution, transfer, incubation in, dialysis against, or other interaction of samples (whether crude samples, sample extracts, or intermediate samples such as supernatants, pellets, interfaces, or extracts thereof) with other agent(s). Such agents include but are not limited to buffers, salts, solvents (e.g., ethanol, isopropanol, methanol, polar solvents, nonpolar solvents), chelating agents, osmotically active agents, acids, bases, proteases, protease inhibitors, nucleases, nuclease inhibitors, antioxidants, etc.

Methods of the present invention are not limited by sample type. Samples may be human or veterinary clinical or research samples (e.g., bodily fluids including but not limited to whole blood, plasma, tissue samples, cell extracts, sputum, saliva, cerebrospinal fluid, etc.; solid biological samples such as bone, muscle, connective tissue, skin, hide, organ, hair, or homogenates or extracts thereof), agricultural samples (e.g., grain, leaf, stein, stalk, root, tuber, etc. or homogenates or extracts thereof), agricultural commodity samples (e.g., stored or milled grain or homogenates or extracts thereof), food products (e.g., processed foods (e.g., nut butters, cereals, granola bars, nacho chips, pasta, processed foods for human consumption, animal food or feed or homogenates or extracts thereof)), or environmental samples (e.g., water, soil, air, building or construction materials, swabbed surface samples, etc.).

Methods of the present invention are not limited by fungal species. Examples of fungal species include but are not limited to species of the genera *Trichoderma, Gliocladium, Aspergillus, Rhizopus, Clostridium, Phanerochaete, Bacillus, Penicillium, Aureobasidium, Humicola, Talaromyces, Chrysosporium, Monilia, Paecilomyces, Neurospora, Pleurotus; Saccharomyces, Zymomonas, Kluyveromyces, Brettanomyces, Pichia, Cancida, Klebsiella, Fabospora, Pachysolen, Mucor, Chalara, Monilia, Trichoderma, Paecilomyces, Erwinia, Fusarium, Histoplasma, Coccidioides, Blastomyces, Paracoccicdioides, Cryptococcus*, and *Piromyces*. Fungal species may be in the phyla Microsporidia, Chytridiomycota, Blastocladiomycota, Neocallimastigomycota, Glomeromycota, Ascomycota, and Basidiomycota.

Methods of the present invention are not limited by the order in which mechanical and enzymatic sample treatment is conducted. In some embodiments, enzymatic treatment is followed by mechanical treatment. In some embodiments, mechanical treatment is followed by enzymatic treatment. In some embodiments, multiple rounds of treatments are conducted (e.g., enzymatic-mechanical-enzymatic; mechanical-enzymatic-mechanical; enzymatic-mechanical-mechanical-enzymatic; or any possible patterned or non-patterned sequence).

In certain embodiments, the present invention provides a method of extracting fungal nucleic acid from a sample, comprising subjecting the sample to enzymatic treatment; subjecting the sample to mechanical treatment: and extracting nucleic acid from the sample. In some embodiments, the enzymatic treatment is a type such as lysostaphin treatment or lyticase treatment. In some embodiments, enzymatic treatment comprises treatment with lysostaphin and lyticase. In some embodiments, the mechanical treatment is a type such as bead beating, grinding, sonication, extrusion, freezing, freeze-thawing, exposure to pressure exceeding 1 atm, exposure to pressure below 1 atm, exposure to temperature above 37 degrees C., exposure to temperature below 10 degrees C., treatment with a hammer mill, treatment with a knife mill, treatment with a ball mill, treatment with a homogenizer, treatment with a chipping machine, treatment with a grinding machine, treatment with an extrusion device, or irradiation. In some embodiments, the mechanical treatment comprises bead beating. In some embodiments, the method further comprises treatment of the sample with protease. In some embodiments, the method further comprises osmotic shock treatment of the sample. In some embodiments, the method further comprises exposure of the sample to sodium hydroxide. In some embodiments, lysostaphin is added to the sample at a final concentration of 0.0125 U per µl of reaction. In some embodiments, lyticase is added to the sample at a final concentration of 0.22 U per µl of reaction. In some embodiments, the method further comprises addition of buffer to the sample. In some embodiments, the buffer is MOPS. In some embodiments, the nucleic acid extraction is performed using a robotic sample handling system. In some embodiments, the nucleic acid is DNA.

In certain embodiments, the present invention provides a kit for the extraction of fungal nucleic acid from a sample, the kit comprising: particles for mechanical treatment of the sample, and at least one enzyme for enzymatic treatment of the sample. In some embodiments, the particles are comprised of materials such as silica, minerals, glass, zirconia (zirconium)/silica, zirconia (zirconium)/yttrium, zirconia (zirconium), polymer (e.g., plastics, polycarbonate), or garnet. In some embodiments, the enzyme is a type such as lysostaphin or lyticase. In some embodiments, the kit further comprises components such as buffer, solvent, protease, water, sample tubes, and/or instructions.

In certain embodiments, the present invention provides a reaction mixture comprising particles for mechanical treatment of said reaction mixture, at least one enzyme, and fungal cells. In some embodiments, the fungal cells are from a filamentous fungal species.

Additional embodiments will be apparent to persons skilled in the relevant art based on the teachings contained herein.

DESCRIPTION OF THE DRAWINGS

FIG. 1 shows an experimental timeline for Experiment 1.

DEFINITIONS

Figure 2:
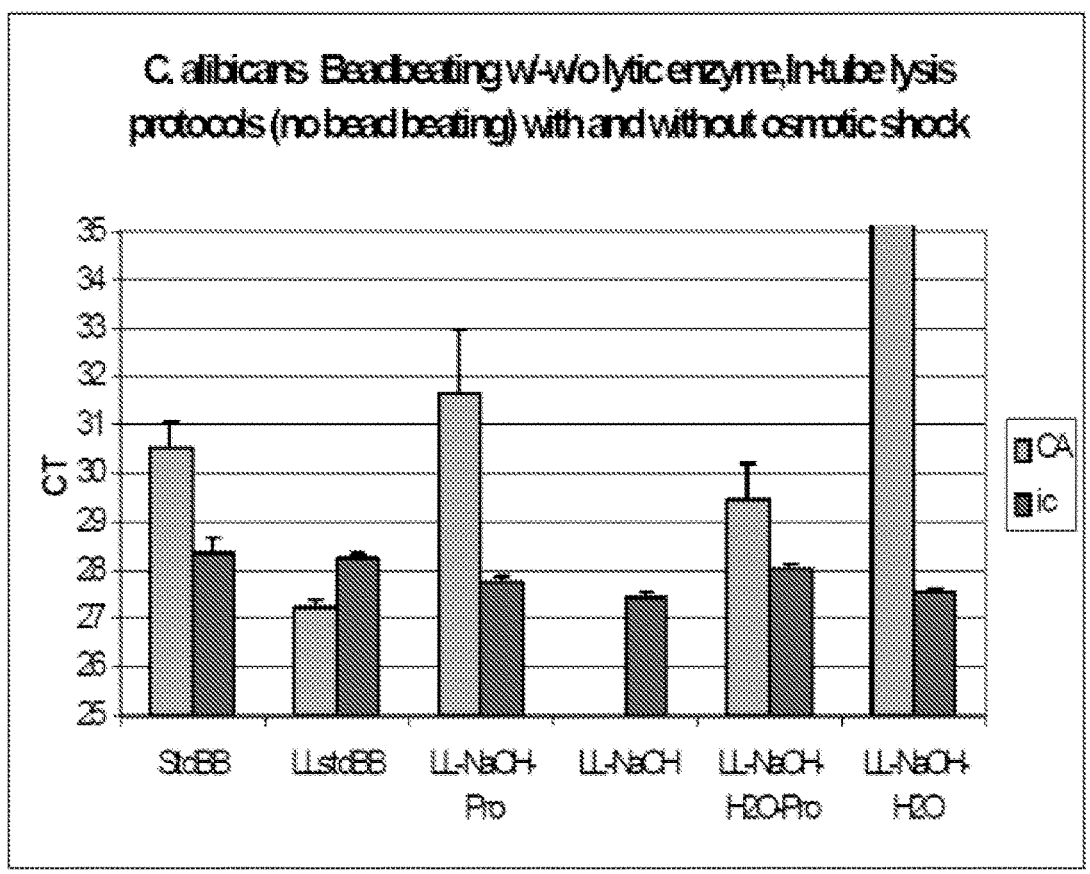
FIG. 2 shows quantitative PCR results for detection of *Candida albicans* DNA from whole blood samples, as described in Experiment 1. CA, *Candida albicans*; IC, internal control.

To facilitate an understanding of the present invention, a number of terms and phrases are defined below:

As used herein, "bead beater" refers to a device that facilitates sample homogenization by mechanical disruption, wherein a vessel containing the sample is held by the device and subjected to agitation, whether by rotating, oscillating, shaking, etc. Typically, particles (e.g., inert particles; also referred to as microparticles or beads) are added to the sample vessel to aid in sample homogenization or maceration.

As used herein, "mechanical treatment", "mechanical processing", "mechanical handling" or similar terms refer to methods of physically disrupting a sample comprising solid material (e.g., a solid sample; a suspension of solids in liquid; a semi-solid (e.g., viscous, gel) sample). Physical effects of mechanical treatment may include but are not limited to reduction of sample particle size, reduction of sample viscosity, liquification, maceration, homogenization, and the like. Examples of mechanical treatment include but are not limited to particle-based disruption (e.g., homogenization using beads, microparticles, and the like, also referred to as bead beating), grinding, sonication, extrusion, freezing, freeze-thawing, high pressure and/or temperature, low pressure and/or temperature, and/or use of hammer mills, knife mills, ball mills, homogenizers (e.g., Dounce homogenizers), chipping machines, grinding machines, extrusion devices, sonication, and/or irradiation.

As used herein, "enzymatic treatment", "enzymatic lysis", "enzymatic processing" or similar terms refer to methods of enzymatic treatment of a sample to achieve physical disruption. Physical effects of enzymatic treatment may include but are not limited to reduction of sample particle size, reduction of sample viscosity, liquification, maceration, homogenization, and the like. In some embodiments, enzymatic treatment achieves disruption of solid biological material (e.g., cell wall). Such disruption may be partial (e.g., increased porosity of cell wall materials; reduced thickness of cell wall material; reduced size of cell wall fragments) or complete.

As used herein, "protease" refers to any enzyme that binds to and cleaves a proteinaceous (e.g., polypeptide, peptide) substrate.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "sample" is used in its broadest sense. In one sense, it is meant to include a specimen or culture obtained from any source, as well as biological and environmental samples. Biological samples may be obtained from animals (including humans), plants, fungi, microbes, etc. and encompass fluids, solids, tissues, and combinations thereof. Biological samples include blood products, such as plasma, serum and the like and tissue samples, such as biopsy samples and the like. Such examples are not however to be construed as limiting the sample types applicable to the present invention.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

DETAILED DESCRIPTION OF THE INVENTION

The invention provides methods for extraction of fungal (e.g., yeast spp., filamentous fungal spp.) nucleic acid (e.g., DNA, RNA). In some embodiments, the present invention provides enhanced nucleic acid extraction from samples comprising fungal cell(s) wherein enzymatic (e.g., lysostaphin, lyticase, or a combination thereof) sample treatment is performed in combination with mechanical (e.g., bead beating) sample treatment.

In experiments conducted during the course of developing some embodiments of the present invention, it was found that pre-treatment of samples (*Candida albicans* or *Staphylococcus aureus* diluted in whole blood) with lyticase and lysostaphin followed by mechanical disruption using bead beating resulted in an eight-fold increase in the amount of fungal DNA extracted, as measured by quantitative PCR.

Accordingly, in some embodiments, the present invention provides methods for extraction of fungal DNA from samples wherein increased yield and/or increased efficiency of nucleic acid extraction is realized.

Mechanical Disruption Methods

The present invention provides methods for fungal nucleic acid extraction from a sample wherein the sample is subjected to mechanical disruption. Types of mechanical disruption include but are not limited to particle-based disruption (e.g., homogenization using beads, microparticles, and the like, also referred to as bead beating), grinding, sonication, extrusion, freezing, freeze-thawing, high pressure and/or temperature, low pressure and/or temperature, and/or use of hammer mills, knife mills, ball mills, homogenizers (e.g., Dounce homogenizers), chipping machines, grinding machines, extrusion devices, French press, and/or irradiation Bead Beating A laboratory-scale mechanical method for cell disruption uses small glass, ceramic, zirconium, or steel beads and a high level of agitation by stirring or shaking of the mix. The method, often referred to as "bead beating", works well for all types of cellular material—from spores to animal and plant tissues.

In some embodiments, beads are added to the cell or tissue suspension in a test tube and the sample is mixed on a common laboratory vortex mixer. While processing time is 3-10 times longer than that in specially machines described herein, it works for easily disrupted cells and is inexpensive.

At a more sophisticated level, bead beating is done in closed vials, centrifuge tubes, or sealed titer plates. The sample and the beads are vigorously agitated (e.g., at about 2000 oscillations per minute) in a specially designed clamp driven by a high energy electric motor. In some machines hundreds of samples can be processed simultaneously. To prevent degradation of biological macromolecules (e.g., DNA, RNA, proteins), some form of cooling is often used because samples experience an increase in heat due to collisions of the beads. Cooling can be accomplished by placing titer plates or vials in chilled aluminum blocks. Another configuration suitable for larger sample volumes uses a rotor inside a sealed 15, 50 or 200 ml chamber to agitate the beads. The chamber can be surrounded by a cooling jacket. Using this same configuration, commercial machines capable of processing many liters of cell suspension are available.

Sonication

A method for cell disruption applies ultrasound (typically 20-50 kHz) to the sample (sonication). In principle, the high-frequency is generated electronically and the mechanical energy is transmitted to the sample via a metal probe that oscillates with high frequency. The probe is placed into the cell-containing sample and the high-frequency oscillation causes a localized low pressure region resulting in cavitation and impaction, ultimately breaking open the cells. Some systems permit cell disruption in smaller samples (including multiple samples under 200 µL in microplate wells) and with an increased ability to control ultrasonication parameters.

Valve-Type Processors

Valve-type processors disrupt cells by forcing the media with the cells through a narrow valve under high pressure (20,000-30,000 psi or 140-210 MPa). As the fluid flows past the valve, high shear forces in the fluid pull the cells apart. By controlling the pressure and valve tension, the shear force can be regulated to optimize cell disruption. Due to the high energies involved, sample cooling is generally required, especially for samples requiring multiple passes through the system. Three major implementations of the technology exist: the French pressure cell press, constant cell disruption systems, and pumped-fluid processors.

French press technology uses an external hydraulic pump to drive a piston within a larger cylinder that contains the sample. The pressurized solution is then squeezed past a needle valve. Once past the valve, the pressure drops to atmospheric pressure and generates shear forces that disrupt the cells.

Cell Bomb

Another system for cell disruption is rapid decompression or the "cell bomb" method. In this process, cells in question are placed under high pressure (usually nitrogen or other inert gas up to about 25,000 psi) and the pressure is rapidly released. The rapid pressure drop causes the dissolved gas to be released as bubbles that ultimately lyse the cell.

Enzymatic Treatment

Lysostaphin

Lysozyme, also known as muramidase or N-acetylmuramide glycanhydrolase, is a family of enzymes (EC 3.2.1.17) which damage bacterial cell walls by catalyzing hydrolysis of 1,4-beta-linkages between N-acetylmuramic acid and N-acetyl-D-glucosamine residues in a peptidoglycan and between N-acetyl-D-glucosamine residues in chitodextrins. Lysozyme is abundant in a number of secretions, such as tears, saliva, human milk and mucus. It is also present in cytoplasmic granules of the polymorphonuclear neutrophils (PMN). Large amounts of lysozyme can be found in egg white. C-type lysozymes are closely related to alpha-lactalbumin in sequence and structure making them part of the same family. Lysostaphin may be produced by recombinant expression (see, e.g., U.S. Pat. No. 4,931,390).

Lyticase (Zymolase, Zymolyase)

Zymolyase (zymolase), also referred to as lyticase, is a preparation of enzymes from *Arthrobacter luteus*. The main activities of the enzyme are β-1,3 glucanase and β-1,3-glucan laminaripentao-hydrolase, which hydrolyze glucose polymers at the β-1,3-glucan linkages releasing laminaripentaose as the principal product. Optimal Zymolyase activity is at 30°-37° C.; lytic activity ceases at higher temperatures. Susceptible fungal genera include but are not limited to *Asbya, Candida, Debaryomyces, Eremothecium, Endomyces, Hansenula, Hanseniaspora, Kloekera, Kluyveromyces, Lipomyces, Metschikowia, Pichia, Pullularia, Saccharomyces, Saccharomycodes, Saccharomycopsis, Schizosaccahromyces*, and *Torulopsis*.

Example

The following example is provided in order to demonstrate and further illustrate certain preferred embodiments and aspects of the present invention and is not to be construed as limiting the scope thereof.

Fungal Nucleic Acid Extraction—Mechanical and Enzymatic Processing

The extraction of *Candida albicans* or *Staphylococcus aureus* DNA present in whole blood samples was performed. Six sets of conditions were used to compare extraction efficiency of mechanical processing (bead beating) alone or in combination with enzymatic treatment (lysostaphin and lyticase) under different osmotic or pH conditions. The combination of enzymatic pre-treatment followed by bead beating was approximately eight-fold more effective than either bead beating or enzymatic treatment performed separately.

Methods and Reagents

DNA was extracted using a DNA extraction kit formulated for the m2000 automated real-time PCR instrument (the mSample Preparation System (DNA) (Abbott Molecular, Abbott Park, Ill.) according to the manufacturer's instructions. Prior to starting, 35 ml of 95% ethanol was added to 70 ml lysis buffer to create wash buffer 2. Lysis buffer was used as wash buffer 1. Microparticles used for bead beating were Zirconia-Silica 9BioSpec). Stock solutions included 5N NaOH (Fisher brand), 1 M MOPS buffer (Sigma brand). Enzyme stock solutions were lysostaphin (2.8 U/µl) which was diluted to 1.4 U/µl with 10 µl used per reaction for a final amount of 14 U per reaction); lyticase at 25 U/µl (used at 250 U per reaction), and proteinase K (Abbott brand). Fungal stocks (*S. aureus* or *C. albicans* at $10^5$/ml) were diluted in whole blood to a final sample concentration of 300 ifu/ml.

Six different extraction conditions were used, with 4 replicates of each condition. Two sets of extraction conditions included bead beating, while 4 did not. For bead beating, 900 mg zirconium/silica beads were used per sample. Extraction condition groups were:

1) standard bead beating extraction (tubes 1-4)
2) Lysostaphin and Lyticase pre-treatment followed by standard bead beating extraction (tubes 5-8)
3) Lysostaphin and Lyticase-NaOH-75 µl water-MOPS (tubes 9-12)
4) Lysostaphin and Lyticase (tubes 13-16)
5) Lysostaphin and Lyticase-NaOH-775 pd water-MOPS (tubes 17-20)
6) Lysostaphin and Lyticase (tubes 21-24)

DNA extraction plates were prepared for nucleic acid preparation using a KingFisher (Thermo Scientific) automated purification system. Extraction plates were prepared as follows:

Loaded 1 ml of Lysis-ethanol into each well of extraction plate.

Added 160 ul of microparticles into each well of extraction plate.
Added extra lysis-ethanol into well that will have extra volume.
For column 3, added 350 ul
For column 4, added 600 ul
For column 5, added 1.5 ml
For column 6, added 1.8 ml
Loaded 2 ml of lysis-ethanol into each well of Wash 1 plate.
Loaded 2 ml of 70% ethanol into each well of Wash 2 plates (all 3)
Loaded 250 ul water into elution plate.

Figure 1:
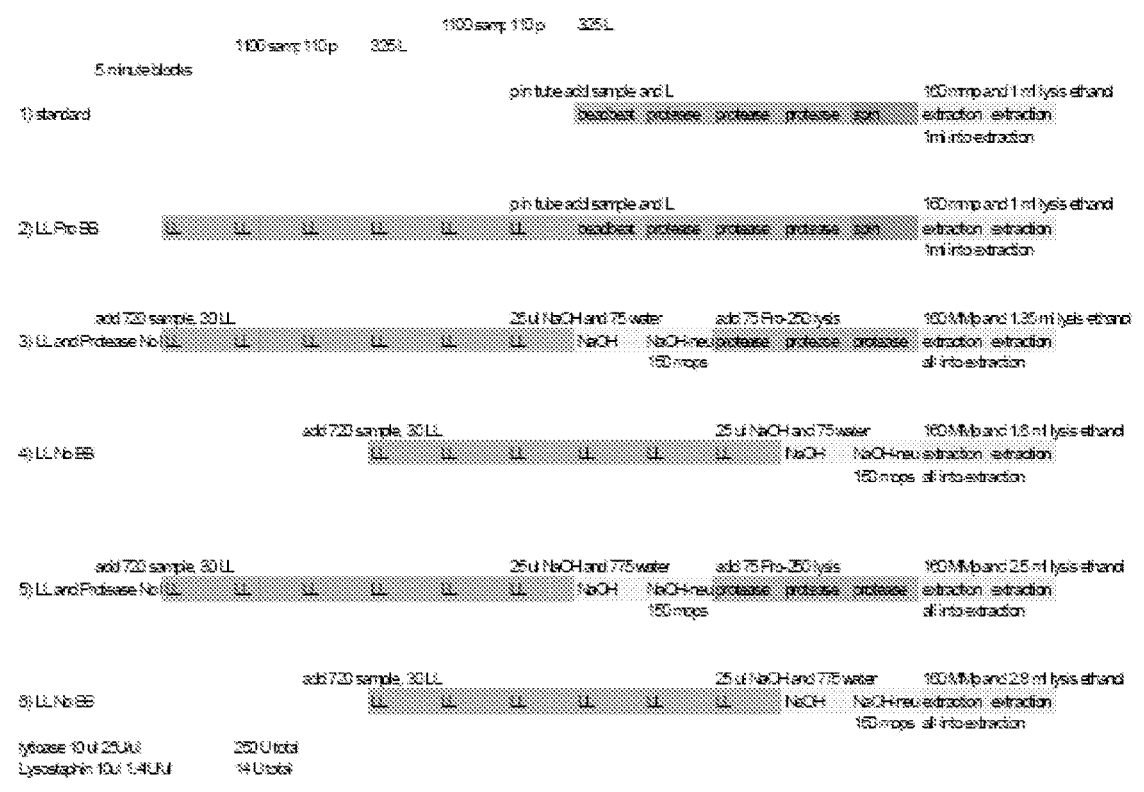

The extraction timeline is shown in FIG. 1. For enzyme treatment samples (groups 2-6), 20 μl enzyme (lysostaphin and lyticase) stock was added to 720 μl sample (groups 3-6) or 1100 μl sample (group 2). Tubes were incubated at 37° C. for 30 min. Group 2 samples (enzyme treatment+bead beating) and Group 1 samples (bead beating only) were subjected to bead beating and incubated at 57° C. for 15 minutes in the presence of 325 μl lysis buffer without ethanol in the presence of 110 μl protease. For samples subjected to sodium hydroxide treatment (groups 3-6), 25 μl of 5N sodium hydroxide was added along with 75 μl water (groups 3 and 4) or 750 μl water (groups 5 and 6). All sodium hydroxide-treated samples were incubated at 57° C. for 10 min, followed by adding 150 μl MOPS buffer and 250 μl lysis buffer. For group 3 and group 5 samples, 75 μl protease was also added. All sodium hydroxide-treated samples (groups 3-6) were then incubated at 57° C. for an additional 15 minutes. Prior to extraction using a KingFisher purification system, all samples were centrifuged and supernatents were loaded on the extraction plate. Extractions were performed with 160 μl magnetic microparticles.

The KingFisher extraction program included a 25 minute drying step at the end to remove traces of ethanol that might otherwise inhibit quantitative PCR. Following extraction, eluates were stored at −20° C.

To assess DNA extraction efficiency, quantitative PCR reactions were carried out:
*C. albicans* assay—for 30 assays
1) Primer 1 0.1 ul/rx, 3 ul total
2) Primer 2 0.1 ul/rx, 3 ul total
3) Probe 0.1 ul/rx 3 ul
4) 2× Taqman Buffer AB #4324018 12.5 ul/rx, 375 ul total
5) 10×IPC mix 2.5 ul/rx, 75 ul total
6) 50×IPC template 0.5 ul/rx, 15 ul total
7) Water. 4.3 ul/rx, 129 ul total
Master mix was made, and add 20 ul was added to each well in the plate. Following this, 5 μl sample was added per reaction. Quantitative PCR was performed and samples were stored at −20° C. when complete.

The *S. aureus* assay was performed identically using target-specific primers and probes.

Figure 3:
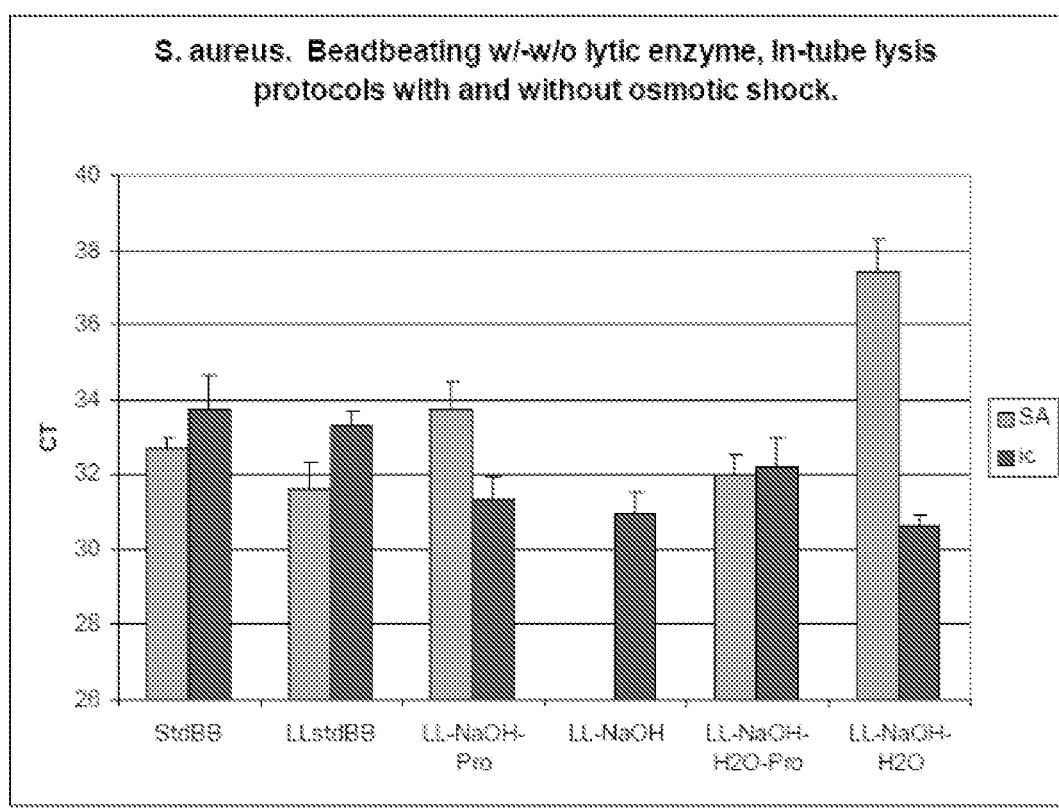
FIG. 3 shows quantitative PCR results for detection of *Staphylococcus aureus* DNA from whole blood samples, as described in Experiment 1. SA, *Staphylococcus aureus*; IC, internal control.

Results are shown below and in FIGS. 2 and 3.

TABLE 1

*C. albicans* assay results.

| Protocol | *C. albicans* assay results | Internal Control | Standard Deviation, *S. aureus* | Standard Deviation, Internal Control |
|---|---|---|---|---|
| Standard bead beating (Group 1) | 30.5425 | 28.3625 | 0.50566 | 0.333504 |
| Lysostaphin and Lyticase + standard bead beating (Group 2) | 27.245 | 28.27 | 0.169017 | 0.069761 |

TABLE 1-continued

*C. albicans* assay results.

| Protocol | *C. albicans* assay results | Internal Control | Standard Deviation, *S. aureus* | Standard Deviation, Internal Control |
|---|---|---|---|---|
| Lysostaphin and Lyticase, NaOH, MOPS (Group 3) | 31.665 | 27.7475 | 1.31272 | 0.140089 |
| Lystostaphin and Lyticase (Group 4) | −1 | 27.47 | 0 | 0.100333 |
| Lysostaphin and Lyticase, NaOH, MOPS (Group 5) | 29.455 | 28.035 | 0.737496 | 0.106301 |
| Lysostaphin and Lyticase (Group 6) | 36.74 | 27.5375 | 1.24503 | 0.074554 |

TABLE 2

*S. aureus* assay results.

| Protocol | *S. aureus* assay results | Internal Control | Standard Deviation, *S. aureus* | Standard Deviation, Internal Control |
|---|---|---|---|---|
| Standard bead beating (Group 1) | 32.71 | 33.7625 | 0.280595 | 0.878725 |
| Lysostaphin and Lyticase + standard bead beating (Group 2) | 31.6125 | 33.3 | 0.737626 | 0.402409 |
| Lysostaphin and Lyticase, NaOH, MOPS (Group 3) | 33.7375 | 31.345 | 0.724724 | 0.635898 |
| Lystostaphin and Lyticase (Group 4) | −1 | 30.9675 | 0 | 0.581112 |
| Lysostaphin and Lyticase, NaOH, MOPS (Group 5) | 32.03 | 32.185 | 0.508789 | 0.814064 |
| Lysostaphin and Lyticase (Group 6) | 37.4675 | 30.6275 | 0.843421 | 0.263486 |

The lysticase-lysostaphin treatment appeared to help the bead beating and gave the best result. Over a 3 CT improvement for the *C. albicans* assay and over a 1 CT improvement for the *S. aureus* assay was observed. This extraction without the bead beating was different in that the NaOH treatment was done prior to the protease treatment. No sample clumping was observed when protease treatment was done before the NaOH treatment. The treatment with the osmotic shock and the protease (no bead beating) worked almost as well as the bead beating with the enzyme for *S. aureus* (0.7 CT improvement). The same protocol had over a 1 CT improvement for the *C. albicans* assay.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology or microbiology are intended to be within the scope of the following claims.

What is claimed is:

1. A method of extracting fungal nucleic acid from a sample, comprising:
    a) treating said sample with enzymatic treatment wherein said enzymatic treatment comprises treatment with lysostaphin and lyticase in a reaction mixture wherein said reaction mixture does not comprise a chelator;
    b) treating said reaction mixture with mechanical treatment: and
    c) extracting said nucleic acid from said reaction mixture wherein a combination of said enzymatic treatment comprising said lysostaphin and said lyticase with said mechanical treatment results in an increased yield of said extracted nucleic acid compared to enzymatic treatment or mechanical treatment performed separately.

2. The method of claim 1 wherein said mechanical treatment is selected from the group consisting of bead beating, grinding, sonication, extrusion, freezing, freeze-thawing, exposure to pressure exceeding 1 atm, exposure to pressure below 1 atm, exposure to temperature above 37 degrees C., exposure to temperature below 10 degrees C., treatment with a hammer mill, treatment with a knife mill, treatment with a ball mill, treatment with a homogenizer, treatment with a chipping machine, treatment with a grinding machine, treatment with a French press, treatment with an extrusion device, and irradiation.

3. The method of claim 1, wherein said mechanical treatment comprises bead beating.

4. The method of claim 1, further comprising treatment of said sample with protease.

5. The method of claim 1, further comprising osmotic shock treatment of said sample.

6. The method of claim 1, further comprising exposure of said sample to sodium hydroxide.

7. The treatment of claim 1, wherein said lysostaphin is added to said sample at a final concentration of 0.0125 U per µl of reaction mixture.

8. The treatment of claim 1, wherein said lyticase is added to said sample at a final concentration of 0.22 U per µl of reaction mixture.

9. The method of claim 1, further comprising addition of buffer to said sample.

10. The method of claim 9, wherein said buffer is MOPS.

11. The method of claim 1, wherein said extracting is performed using a robotic sample handling system.

12. The method of claim 1, wherein said nucleic acid is DNA.

* * * * *

UNITED STATES PATENT AND TRADEMARK OFFICE
CERTIFICATE OF CORRECTION

PATENT NO.            : 10,041,061 B2
APPLICATION NO.       : 13/876144
DATED                 : August 7, 2018
INVENTOR(S)           : Gerard Gundling et al.

Page 1 of 1

It is certified that error appears in the above-identified patent and that said Letters Patent is hereby corrected as shown below:

In the Claims

Claim 7, Column 12, Line 18 reads:
"The treatment of claim 1, wherein said lysostaphin is"
Whereas it should read:
"The method of claim 1, wherein said lysostaphin is"

Claim 8, Column 12, Line 21 reads:
"The treatment of claim 1, wherein said lyticase is added"
Whereas it should read:
"The method of claim 1, wherein said lyticase is added"

Signed and Sealed this
Ninth Day of October, 2018

Andrei Iancu
*Director of the United States Patent and Trademark Office*